United States Patent
Ellis et al.

(10) Patent No.: US 7,745,675 B2
(45) Date of Patent: Jun. 29, 2010

(54) REGENERATION OF PLATINUM-GERMANIUM ZEOLITE CATALYST

(75) Inventors: Paul E. Ellis, Sugar Land, TX (US); Gopalakrishnan G. Juttu, Sugar Land, TX (US); Alla K. Khanmamedova, Sugar Land, TX (US); Scott F. Mitchell, The Woodlands, TX (US); Scott A. Stevenson, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 829 days.

(21) Appl. No.: 11/642,421

(22) Filed: Dec. 20, 2006

(65) Prior Publication Data
US 2008/0154079 A1 Jun. 26, 2008

(51) Int. Cl.
*C07C 2/42* (2006.01)
*B01J 38/42* (2006.01)
*B01J 38/44* (2006.01)
*B01J 38/10* (2006.01)

(52) U.S. Cl. .................. 585/418; 585/419; 585/904; 502/35; 502/37; 502/38; 502/53; 502/55

(58) Field of Classification Search .............. 585/418, 585/419, 904; 502/35, 37, 38, 53, 55
See application file for complete search history.

(56) References Cited

U.S. PATENT DOCUMENTS

| 4,806,699 | A | 2/1989 | Smith et al. |
|---|---|---|---|
| 5,019,663 | A | 5/1991 | Chou et al. |
| 5,155,074 | A | 10/1992 | Mohr |
| 5,155,075 | A | 10/1992 | Innes et al. |
| 5,157,183 | A | 10/1992 | Cotterman et al. |
| 5,157,201 | A | 10/1992 | Norris |
| 6,040,259 | A | 3/2000 | Mohr et al. |
| 6,420,295 | B1 | 7/2002 | Wu et al. |
| 6,784,333 | B2 | 8/2004 | Juttu et al. |

*Primary Examiner*—Thuan D Dang
(74) *Attorney, Agent, or Firm*—Jim Wheelington

(57) ABSTRACT

This invention relates to a process for regeneration of a zeolite catalyst, specifically an aluminosilicate zeolite with germanium substituted in the framework for silicon and with platinum deposited on the zeolite. The catalyst may be used in a process for aromatization of alkanes, specifically $C_2$-$C_8$ alkanes. The regeneration process 1) removes coke and sulfur from the catalyst via oxidation, 2) redisperses platinum on the surface of the catalyst via chlorine gas, 3) removes chlorine and bind Pt to the surface of the zeolite by steaming, 4) reduces the catalyst in hydrogen, and 5) optionally, resulfides the catalyst. The zeolite may be a MFI zeolite. The catalyst may be bound with an inert material which does not act as a binding site for platinum during the regeneration process, for example, silica.

60 Claims, 9 Drawing Sheets

REGENERATION OF PLATINUM-GERMANIUM ZEOLITE CATALYST

BACKGROUND OF THE INVENTION

1. Field of the Invention

This invention relates to a process for regeneration of a zeolite catalyst, specifically an aluminosilicate zeolite with germanium substituted in the framework for silicon and with platinum deposited on the zeolite. The catalyst may be used in a process for aromatization of alkanes, e.g. $C_2$-$C_8$.

2. Description of the Prior Art

Zeolites are a crystalline hydrated aluminosilicate that may also contain other metals. The term "zeolite" includes not only aluminosilicates but substances in which the aluminum is replaced by other trivalent elements and substance in which silicon is replaced by other tetravalent elements. Elements may be deposited on the zeolite to enhance properties of a zeolite catalyst used in particular processes.

Zeolites are known catalysts for aromatics in isomerization, toluene disproportionation, transalkylation, hydrogenation and alkane oligomerization and aromatization. Generally, catalysts deactivate when operated under commercial process conditions and must be regenerated to continue to be used in a reaction system.

U.S. Pat. No. 4,806,699 discloses a process for the production of aromatic hydrocarbons from ethane and/or propane and/or butane with a gallium loaded ZSM-5 type aluminosilicate zeolite which is regenerated using a conventional method, e.g. by burning off the deactivating carbon deposited thereon using air diluted with an inert gas, e.g., nitrogen at elevated temperature.

U.S. Pat. No. 5,019,663 discloses aromatization of $C_3$-$C_4$ paraffin-rich streams (commonly known as LPG), in a highly endothermic reaction in a fixed, moving or fluid catalyst bed. For example, the CYCLAR (tradename) process for LPG aromatization uses a plurality of moving-bed reaction zones together with continuous catalyst regeneration (CCR) to supply the required heat for the primary endothermic reaction. This commercial process scheme involving transporting hot catalyst pellets between the reaction and regeneration zones requires extensive capital investment. The CYCLAR (tradename) process is described in the paper "CYCLAR: One Step Processing of LPG to Aromatics and Hydrogen," by R. F. Anderson, J. A. Johnson and J. R. Mowry presented at the AIChE Spring National Meeting, Houston, Tex., Mar. 24-28, 1985.

U.S. Pat. No. 5,155,075 discloses a process for regeneration of a hydrocarbon reforming catalyst which has been deactivated by buildup of coke. The catalyst is regenerated by a controlled low temperature carbon-burn procedure. In the reactor design, catalyst that is still active, but which has some coke buildup is slowly withdrawn from the bottom of the last reactor stage and transferred to the regeneration section while an equivalent volume of regenerated catalyst is conveyed from the regenerator back to the top of the first reactor. Regeneration consists of the combustion of the deposited coke using high temperature air and/or steam.

U.S. Pat. No. 5,157,183 discloses a process for converting low molecular weight non-aromatic compounds into higher molecular weight aromatic compounds utilizing a nickel-promoted zeolite catalyst with a $SiO_2/Al_2O_3$ ratio greater than 5. The nickel zeolite catalyst is subjected to thermal or hydrothermal treatments which results in a decrease in the amount of carbon deposited and a catalyst which resists thermal degradation of regeneration and retains a greater portion of its original activity even after several regenerations.

U.S. Pat. No. 6,420,295 discloses a catalyst composition for use in converting hydrocarbons of a mixture of a zeolite and a binder that has first been calcined and then combined with a promoter compound in the presence of a complexing ligand. The binder is silica or alumina, the promoter compound contains zinc and the complexing liquid is ethylenediaminetetraacetic acid or a salt thereof. A regeneration procedure calcining in air to burn off deposited coke and other carbonaceous materials, such as oligomers or polymers, preferably at a temperature of about 300 to about 1000° C. The optimal time periods of the calcining depend generally on the types and amounts of deactivating deposits on the catalyst composition and on the calcination temperatures.

SUMMARY OF THE INVENTION

An aluminum-silicon-germanium zeolite on which platinum has been deposited used in a process for aromatization of alkanes is regenerated by 1) removing coke and sulfur via oxidation, 2) redispersing platinum via a chlorine containing gas stream, 3) steaming to remove chlorine and bind Pt to the surface of the zeolite, and 4) reducing in hydrogen. The regenerated catalyst may be treated with sulfur (sulfided) prior to reuse in a process for aromatization of alkanes. In one embodiment of the invention the zeolite structure is ZSM-5 MFI zeolite. In another embodiment of the invention the catalyst is bound with an inert material which does not act as a binding site for platinum during the regeneration process. One example of the binding material is silica. In one embodiment the invention is used in a process for aromatization of $C_2$-$C_8$ alkanes. In another embodiment the invention is used in a process for aromatization of $C_2$-$C_4$ alkanes.

The invention is for a process for regenerating a catalyst containing an aluminum-silicon-germanium zeolite on which platinum has been deposited comprising:

a) a contacting the catalyst first with a gaseous stream containing chlorine or a chlorine-containing compound, water and oxygen at partial pressures of about 0.014 psia to about 0.094 psia, about 0 psia to about 0.75 psia and about 0.14 psia to about 0.94 psia, respectively;

b) contacting the catalyst second with a gaseous stream containing chlorine or a chlorine-containing compound, water and oxygen at partial pressures of about 0.014 psia to about 0.094 psia, about 0.015 psia to about 0.75 psia and about 0.2 psia to about 2.24 psia, respectively, wherein the partial pressure of oxygen in step 2) is higher than the partial pressure of oxygen in step 1);

c) contacting the catalyst thirdly with a gaseous stream containing chlorine or a chlorine containing compound, water and oxygen at partial pressures of about 0.029 psia to about 0.37 psia, about 0 psia to about 0.19 psia and about 0.2 psia to about 2.24 psia, respectively, wherein the partial pressure of chlorine in step 3) is higher than the partial pressure of chlorine in step 2);

d) steaming the catalyst with oxygen and water at partial pressures of about 0.2 psia to about 2.24 psia and about 0.029 psia to about 0.75 psia, respectively; and e) reducing the catalyst in hydrogen at a partial pressure of about 0.7 to about 19.7 psia.

The invention may be used in a process for the aromatization of hydrocarbons comprising:

a) contacting a feedstock of one or more alkane(s) containing 2 to 8 carbon atoms per molecule ($C_2$-$C_8$) with at least one catalyst containing an aluminum-silicon-germanium zeolite on which platinum has been deposited;

b) recovering the aromatic product; and c) regenerating the catalyst.

The feedstock may be one or more alkane(s) containing 2 to 4 carbon atoms per molecule ($C_2$-$C_4$) or one or more alkane(s) containing 6 to 8 carbon atoms per molecule ($C_6$-$C_8$).

BRIEF DESCRIPTION OF THE DRAWINGS

A more complete appreciation of the invention and many of the attendant advantages thereof will be readily understood by reference to the following detailed description when considered in connection with the accompanying drawings.

DETAILED DESCRIPTION OF THE INVENTION

As disclosed in U.S. Pat. No. 6,784,333, an aluminum-silicon-germanium zeolite on which platinum has been deposited has been found to be useful in a process for the aromatization of hydrocarbons with relatively constant selectivity for conversion of lower alkanes to aromatics, e.g., alkanes having two to six carbon atoms per molecule to benzene, toluene and xylenes.

Zeolites are known to be crystallized aluminosilicates and include structures of $TO_4$ tetrahedra, which form a three dimensional network by sharing oxygen atoms where T represents tetravalent silicon and trivalent aluminum. The Si/Al ratio for the present invention is in excess of 35:1, with one embodiment of the invention having a Si/Al ratio from 35 to 60 and another embodiment of the invention having a Si/Al ratio from 45 to 55. Trivalent elements may be substituted for the aluminum and tetravalent elements may be substituted for the silicon. In the present invention, germanium has been introduced into the aluminosilicate framework of the zeolite. The silicon/germanium to aluminum atomic ratio (Si—Ge:Al) of the MFI zeolite is preferably greater than 25:1, more preferably in the range from 45:1 to 250:1, and most preferably in the range from 50:1 to 100:1. The zeolite structure may be of MFI, FAU, TON, MFL, VPI, MEL, AEL, AFI, MWW or MOR, but preferably, the zeolite has a MFI structure, more preferably is an MFI aluminum-silicon-germanium zeolite.

The typical technique for synthesizing zeolites comprises converting an amorphous gel to zeolite crystals by a hydrothermal process, employing a dissolution/recrystallization mechanism. The reaction medium also contains structuring agents which are incorporated in the microporous space of the zeolite network during crystallization, thus controlling the construction of the network and assisting to stabilize the structure through the interactions with the zeolite components.

Platinum is deposited on the zeolite by any known method of depositing a metal on a zeolite. Typical methods of depositing a metal on zeolite are ion exchange and impregnation. In one embodiment of the invention platinum is present in the range from 0.05% to 3% by weight. In another embodiment of the invention platinum is present in the range from 0.2% to 2% by weight. In another embodiment of the invention platinum is present in the range from 0.2 to 1.5% by weight.

The aluminum-silicon-germanium zeolite on which platinum has been deposited it believed to be applicable for a wide range of conversion processes which use catalysts to convert a hydrocarbonaceous feed, i.e., a feed containing hydrocarbons, all or in part, such as isomerization, toluene disproportionation, transalkylation, hydrogenation and alkane oligomerization and aromatization. These processes and the useful range of process conditions are all well known in the art. One example of use of the zeolite catalyst of the present invention is for aromatization of alkanes to aromatics, e.g., benzene, toluene and xylenes (BTX). In one embodiment of the invention the alkane is selected from one or more $C_2$-$C_8$ alkanes. In another embodiment of the invention the alkane is selected from one or more $C_2$-$C_4$ alkanes. In another embodiment of the invention the alkane is selected from one or more $C_6$-$C_8$ alkanes.

One example of an aromatization process is the Cyclar™ process which converts liquefied petroleum gas (LPG) directly into a liquid aromatics product in a single operation. LPG consists mainly of propane and butane but can also contain $C_2$, $C_5$ and $C_6$ alkanes and $C_2$-$C_6$ olefins. LPG, which is primarily recovered from gas and oil fields and petroleum refining operations, is relatively low in value and is available in abundance, qualities which make it a good feedstock for petrochemical applications, such as aromatization. The Cyclar process is described as dehydrocyclodimerization, which is a sequential dehydrogenation of $C_3$ and/or $C_4$ alkanes to olefins, oligomerization of the olefins, cyclization to naphthenes and dehydrogenation of naphthenes to corresponding aromatics. Hydrocracking side reactions of the olefins and oligomers generate methane and ethane. The dehydrogenation reactions generate hydrogen Commercial alkane aromatization processes are generally continuous. Over time the catalyst is deactivated and the productivity (weight of aromatics per weight of catalyst per hour) decreases. Catalyst regeneration is preferable to a one-time use catalyst. For a zeolite-based catalyst in an alkane aromatization reaction, the catalyst is deactivated by formation of coke and other carbon-based materials. Catalyst deactivation is a subjective determination of loss of activity and the catalyst can be regenerated at any point after the catalytic reaction has begun. As noted in the discussion of prior art above, the conventional method to remove coke is to burn off the coke and other carbon based material deposited on the catalyst at elevated temperatures. Coke is generally in two forms: labile in which the carbonaceous species contains multiple C—H bonds and graphitic in which carbon is bonded predominately to other to carbons. Labile coke is easier to remove than graphite coke. Graphitic coke makes up about 3-5% by weight of the total coke. When labile coke ($C_xH_y$ where x and y are integers) is removed or burned, it produces $CO_{x'}$ and $H_2O$ where x' is 1 or 2.

Figure 1:
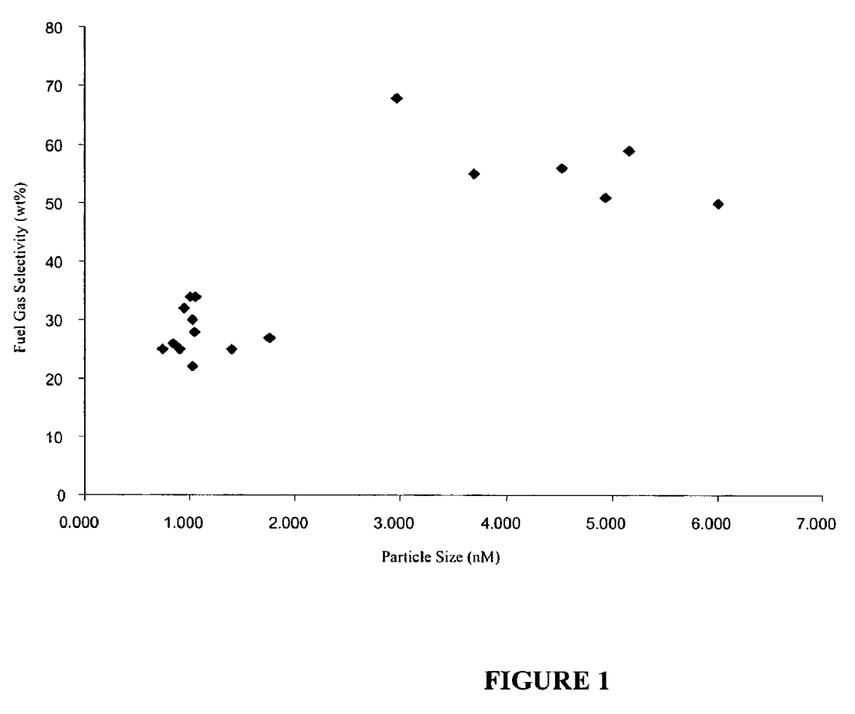
FIG. 1 shows the effect of platinum particle size on fuel gas selectivity

For zeolite-based catalysts on which platinum is deposited, the temperatures of the alkane aromatization reaction and, especially, elevated temperatures of a conventional regeneration procedure cause the platinum to "sinter", i.e., platinum particles agglomerate resulting in an increase of platinum particle size on the surface of the zeolite. Sintering causes a loss of metal surface area and catalyst performance, specifically selectivity (see FIG. 1).

It would be advantageous to have a regeneration procedure which removes the coke and other carbon-based materials that contribute to the deactivation of the catalyst and which also retains dispersion of the platinum on the surface of the zeolite. The regeneration procedure of the present invention incorporates coke removal and redispersion of the platinum. The procedure of the present invention should be applicable for regeneration of a catalyst of aluminum-silicon-germanium zeolite on which platinum has been deposited which has become deactivated in a conversion process of a hydrocarbonaceous feed, e.g., isomerization, toluene disproportionation, transalkylation, hydrogenation and alkane oligomerization and aromatization.

The regeneration procedure involves five separate stages and an optional sixth stage. The first stage uses oxygen and chlorine as reactants in the optional presence of water which is a product of the reaction. The second stage also uses oxygen and chlorine as reactants but with a relatively higher concentration of oxygen. Water may be present since it is a product of the reaction and the concentration of water may also be higher than in the previous stage due to carryover of reaction product water generated in the previous stage. The third stage also uses oxygen and chlorine as reactants but with relatively higher concentrations of chlorine relative to the previous stage. Water may also be present due to carryover from the previous stages. The fourth stage is a "steaming" phase that subjects the catalyst to relatively high concentrations of both oxygen and water. The catalyst is activated by being reduced in a hydrogen containing stream. The catalyst may be sulfided before beginning another process reaction.

It is believed that the first two stages remove coke while limiting platinum agglomeration, the third stage disperses Pt, the steaming removes chlorine and binds Pt to the surface of the zeolite but it is not suggested that no other actions occur during each stage. Pt may be dispersed during the first two stages and coke may be removed during the third stage, etc. Furthermore, even though water is produced when coke is burned, water may participate in the reactions of the regeneration process, specifically the redispersion of the platinum, and the amount of water present may be adjusted by removal or addition of water.

The particular concentrations, times and temperatures at each stage can be adjusted depending on the degree of deactivation of the catalyst and the type and amount of carbon-based materials that contribute to the deactivation. Typical ranges for concentrations (partial pressures at an operating pressure up to 4 psig, flow of 1000-8000 GHSV), times and temperatures for regenerating a 2 gram sample of catalyst are as follows: In the first stage, the partial pressures of chlorine, water and oxygen are about 0.014 psia to about 0.094 psia, about 0 psia to about 0.75 psia and about 0.14 psia to about 0.94 psia, respectively. The reaction in the first stage may be at a temperature from about 400 to about 550° C. for about 50 minutes to about 24 hours. In the second stage, the partial pressures of chlorine, water and oxygen are about 0.014 psia to about 0.094 psia, about 0.015 psia to about 0.75 psia and about 0.2 psia to about 2.24 psia, respectively. The partial pressure of oxygen in the second stage is higher than the partial pressure of oxygen in the first stage. The reaction in the second stage may be at a temperature from about 400° C. to about 550° C. for about 60 minutes to about 24 hours. In the third stage, the partial pressures of chlorine, water and oxygen are about 0.029 psia to about 0.37 psia, about 0 psia to about 0.19 psia and about 0.2 psia to about 2.24 psia, respectively. The partial pressure of chlorine in the third stage is higher than the partial pressure of chlorine in the second stage. The reaction in the third stage may be at a temperature in the range from about 400 to about 550° C. for about one hour to about 48 hours. In the fourth stage, the partial pressures of oxygen and water are about 0.2 psia to about 2.24 psia and about 0.029 psia to about 0.75 psia, respectively. The reaction in the fourth stage may be at a temperature in the range from about 200° C. to about 550° C. for about 15 minutes to about 12 hours. In the fifth stage, the partial pressure of hydrogen is about 0.7 to about 19.7 psia. The reaction in the fifth stage may be at a temperature in the range from 200° C. to 550° C. for about 30 minutes to twenty-four hours.

In another embodiment of the present invention, in the first stage, the partial pressures of chlorine, water and oxygen are about 0.014 psia to about 0.06 psia, about 0 psia to about 0.6 psia and about 0.14 psia to about 0.6 psia, respectively. The reaction in the first stage may be at a temperature from about 425 to about 540° C. for about 50 minutes to about 20 hours. In the second stage, the partial pressures of chlorine, water and oxygen are about 0.014 psia to about 0.06 psia, about 0.15 psia to about 0.6 psia and about 0.2 psia to about 2.0 psia, respectively. The reaction in the second stage may be at a temperature from about 425° C. to about 540° C. for about 1 hour to about 20 hours. In the third stage, the partial pressures of chlorine, water and oxygen are about 0.05 psia to about 0.3 psia, about 0.0 psia to about 0.15 psia and about 0.2 psia to about 2.0 psia, respectively. The reaction in the third stage may be at a temperature in the range from about 425 to about 540° C. for about three hours to twenty-four hours. In the fourth stage, the partial pressures of oxygen and water are about 0.5 psia to about 2.0 psia and about 0.15 psia to about 0.6 psia, respectively. The reaction in the fourth stage may be at a temperature in the range from about 425° C. to about 540° C. for about 30 minutes to about 10 hours. In the fifth stage, the partial pressure of hydrogen is about 0.7 to about 19.0 psia. The reaction in the fifth stage may be at a temperature in the range from 425° C. to 540° C. for about 30 minutes to about eighteen hours.

In another embodiment of the present invention, in the first stage, the partial pressures of chlorine, water and oxygen are about 0.014 psia to about 0.04 psia, about 0 psia to about 0.04 psia and about 0.14 psia to about 0.4 psia, respectively. The reaction in the first stage may be at a temperature from about 450 to about 525° C. for about 1 hour to about 16 hours. In the second stage, the partial pressures of chlorine, water and oxygen are about 0.014 psia to about 0.04 psia, about 0.15 psia to about 0.4 psia and about 0.4 psia to about 2.0 psia, respectively. The reaction in the second stage may be at a temperature from about 450° C. to about 525° C. for about 1 hour to about sixteen hours. In the third stage, the partial pressures of chlorine, water and oxygen are about 0.1 psia to about 0.25 psia, about 0.0 psia to about 0.1 psia and about 0.4 psia to about 1.5 psia, respectively. The reaction in the third stage may be at a temperature in the range from about 450 to about 525° C. for about three hours to about eighteen hours. In the fourth stage, the partial pressures of oxygen and water are about 0.75 psia to about 1.75 psia and about 0.15 psia to about 0.4 psia, respectively. The reaction in the fourth stage may be at a temperature in the range from about 450° C. to about 525° C. for about thirty minutes to about 8 hours. In the fifth stage, the partial pressure of hydrogen is about 0.8 to about 15.0 psia. The reaction in the fifth stage may be at a temperature in the range from 450° C. to 525° C. for about 30 minutes to about twelve hours.

The preceding ranges for partial pressures, time and temperatures should be applicable for a wide range of amounts and weights of catalyst. The following guidelines can be used to modify or optimize process condition variables. A temperature control set point in the ranges specified above may be set at the beginning of the first step in the reactor. The oxidation reaction of the coke, i.e., coke+$O_2$→$CO_x$, is an exothermic reaction which generates heat and increases the temperature of the catalyst above the set point. As coke is burnt off, the temperature decreases and the amount of time in the first stage is determined by the reduction in exothermicity which reflects the reduction in production of $CO_x$ as the temperature of the catalyst approaches the control set point. In the second step, most of the remaining coke is burnt off by a second oxidation reaction of the coke in which the production of $CO_x$ and the concentration of $O_2$ are monitored. $CO_x$ may be monitored as explained for the first step. When the difference between $O_2$ concentrations of feed and of exit approaches zero, the catalyst will be maintained within the temperature range for a period of time, e.g., at least two hours, during and after which the $CO_x$ level will be assumed to be at, near or approaching zero. For the third step, the time and temperature ranges specified above should be sufficient with variation within routine experimentation to produce comparable results disclosed herein. The pH of the effluent liquid determines completion of the fourth step. When the pH is approximately neutral, i.e., about 6-8, or, e.g., about 7, washing may be discontinued. For the fifth step, the time and temperature ranges specified above should be sufficient with variation within routine experimentation to produce comparable results disclosed herein.

The regenerated catalyst may be sulfided before use in a process for hydrocarbon conversion by contacting the regenerated catalyst with a sulfur compound, such as hydrogen sulfide or and organosulfide compound, such as dimethyl disulfide, at a gas hourly space velocity [GHSV-volume of gas per volume of catalyst per hour($hr^{-1}$)] of about 10 $hr^{-1}$ to about 8000 $hr^{-1}$ at a temperature range of about 25° C. to about 550° C., e.g. 400° C., until there is detectable breakthrough of sulfur and contacting the sulfided catalyst with a stripping gas, such a hydrogen, or a mixture of a stripping gas with an inert gas, such as nitrogen, argon or helium, at a gas hourly space velocity of about 10 $hr^{-1}$ to about 8000 $hr^{-1}$ at a temperature of about 25° C. to about 550° C., e.g., 100° C. The mixture of stripping gas with inert gas may be in a mole/mole ratio of from about 1/99 to about 100/0, e.g. about 50/50. The sulfur compound may be contacted with the regenerated catalyst as part of the feedstock of the hydrocarbon conversion process. The detectable breakthrough of sulfur may be analyzed by any known means of analyzing for hydrogen sulfide, such as a lead acetate indicator. The preceding ranges for concentrations and temperatures for a 2 gm sample should be applicable for a wide range of amounts and weights of catalyst. Process conditions may be modified or optimized to produce an amount of sulfur on the catalyst as desired, e.g., in the range of from 10 ppm to 0.1 wt. %.

The catalyst may be bound to or supported on oxides of magnesium, aluminum, germanium, titanium, zirconium, thorium, silicon, boron and mixtures thereof. In one embodiment of the invention, the binding material or support is an inert material which does not attract platinum during the regeneration process. Examples of such binding material or support are silica, sulfated alumina, clay or zeolite. The catalyst is bound to the binding material through any known method in the art. Procedures for binding zeolite are well known and are hereby incorporated by reference. Such binding procedures include the oil drop method. The zeolite to binder weight ratio may vary between 20 wt % to 80 wt %.

The invention having been generally described, the following examples are given as particular embodiments of the invention and to demonstrate the practice and advantages thereof. It is understood that the examples are given by way of illustration and are not intended to limit the specification or the claims to follow in any manner.

Catalysts were synthesized and used in a process for aromatization of alkanes by the methods disclosed in U.S. Pat. No. 6,784,333, hereby incorporated by reference. The catalyst was run with a propane feed at 1 LHSV, 22 psig and 500° C. When the catalyst became deactivated, i.e., time onstream of about 70 to about 120 hours and a loss of about 10% to about 20% conversion, it was regenerated as follows:

The catalyst was placed in a 13 mm O.D. X 21" length tube composed of quartz in a hood at a temperature between 450-550° C. and a pressure kept nominally at atmospheric. A quartz frit approximately 6" from the exit of the tube was used to hold the catalyst within the reaction zone. An electric furnace was used to heat the reactor. The thermocouple for the temperature controller was placed outside of the reactor, in the furnace. The furnace temperature limit was set to 600° C. Pressure regulators stepped down the feed pressure to 4 psig. Mass flow controllers regulated the flow of all gases except the chlorine-containing gases which were regulated by rotometer control. The catalyst was regenerated at the following conditions:

| Stage | Duration (min) | $Cl_2$ (psia) | $O_2$ (psia) | $H_2O$ (psia) | $H_2$ (psia) |
|---|---|---|---|---|---|
| 1 | 120 | 0.0374 | 0.374 | 0.0374 | — |
| 2 | 180 | 0.0374 | 1.87 | 0.374 | — |
| 3 | 180 | 0.187 | 1.40 | 0.0374 | — |
| 4 | 60 | — | 1.87 | 0.374 | — |
| 5 | 60 | — | — | — | 0.935 |

The regenerated catalyst was evaluated in a process for aromatization of propane with a propane feed at 1 LHSV, 22 psig and 500° C.

Figure 2:
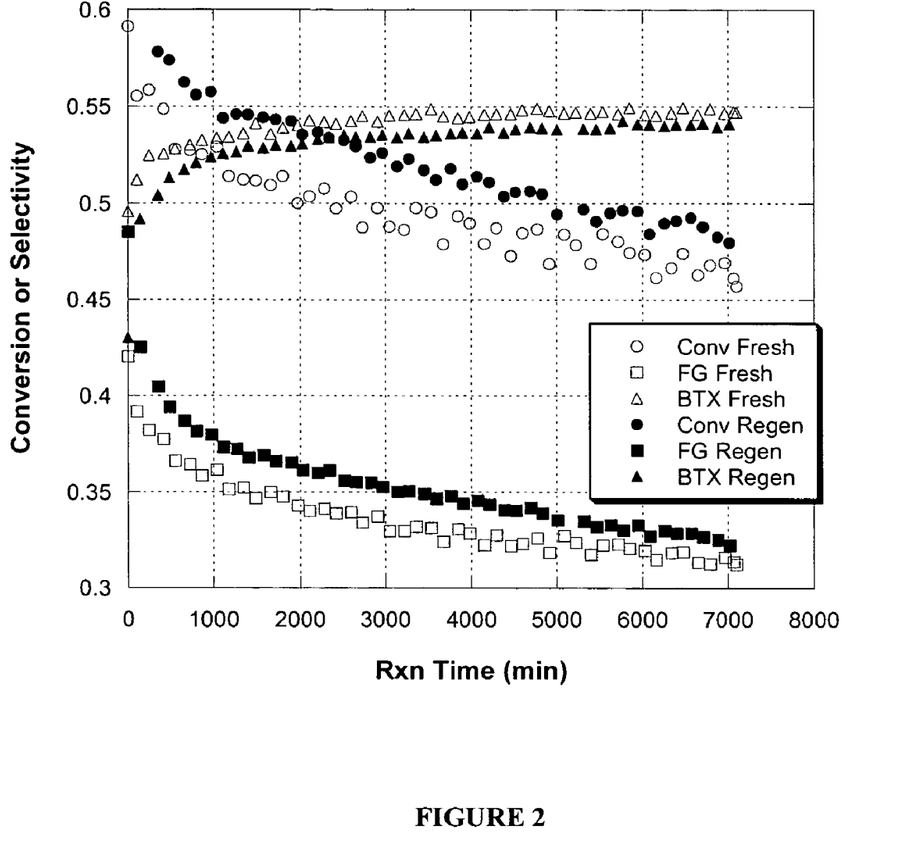
FIG. 2 compares conversion, BTX selectivity and fuel gas selectivity of a silica bound catalyst, fresh and regenerated

As can be seen in FIG. 2, the regenerated catalyst has stable selectivity for benzene-toluene-xylenes (BTX).

Figure 3:
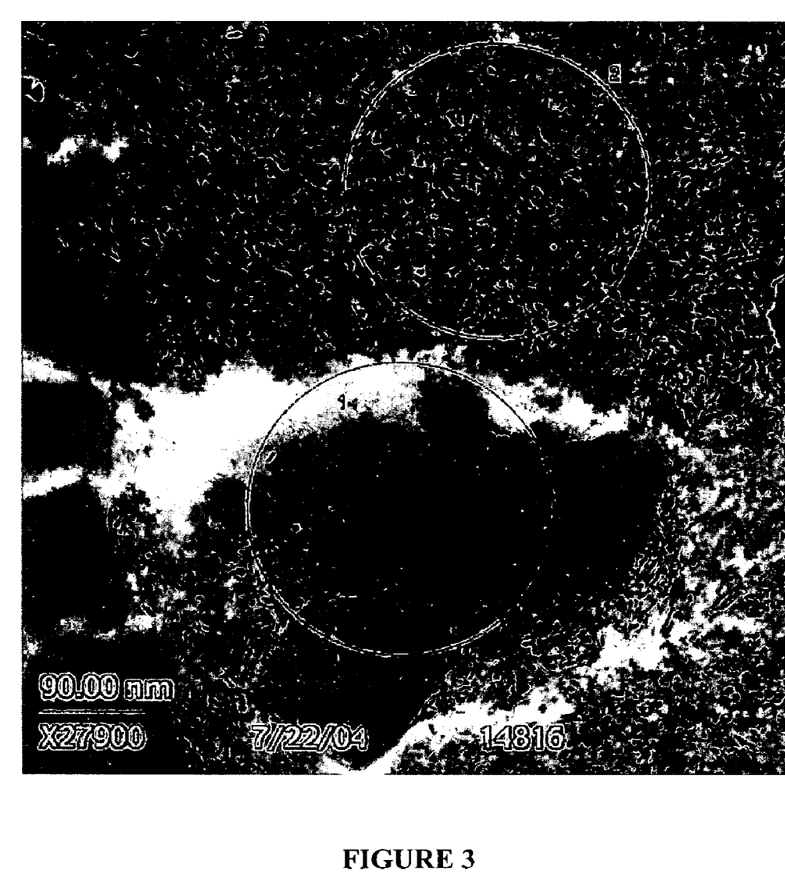
FIG. 3 is a TEM for an alumina bound catalyst
Figure 4:
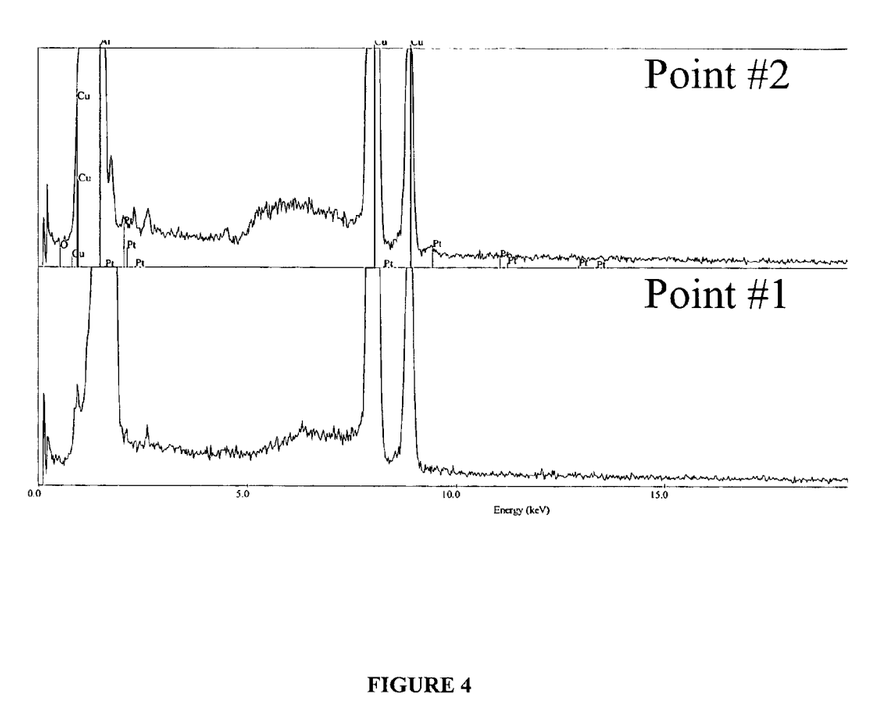
FIG. 4 is a corresponding EDS spectra for the points studied in FIG. 2
Figure 5:
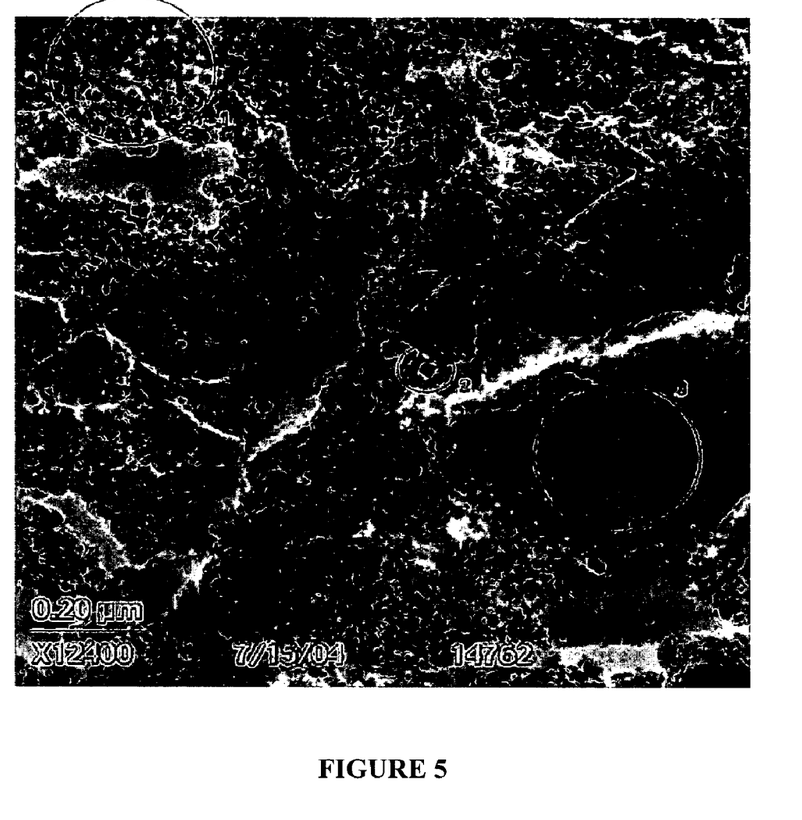
FIG. 5 is a TEM for a silica bound catalyst
Figure 6:
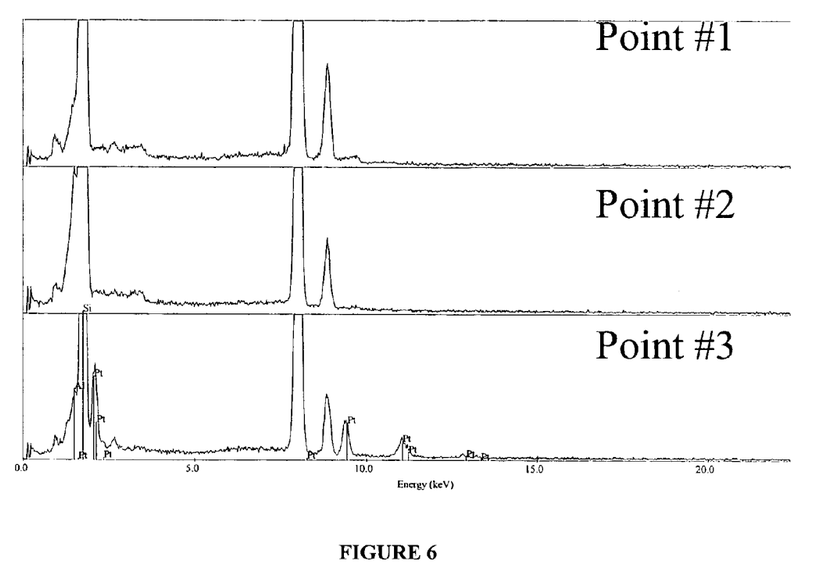
FIG. 6 is a corresponding EDS spectra for the points studied in FIG. 4

Pt—Ge/ZSM-5 catalysts were synthesized by the methods disclosed in U.S. Pat. No. 6,784,333, hereby incorporated by reference, and bound to silica or alumina. The catalysts were bound to silica in a 50/50 weight ratio. The bound catalysts were evaluated in a process for aromatization of propane with a propane feed at 1 LHSV, 22 psig and 500° C. and regenerated at the conditions described above. The catalysts were analyzed by Transmission Electron Microscope (TEM) and Energy Dispersive X-Ray Spectrometry (EDS). The TEM and corresponding EDS spectra for the points studied for the alumina bound catalyst are in FIGS. 3 and 4. The TEM and corresponding EDS spectra for the points studied for the silica bound catalyst are in FIGS. 5 and 6.

For the alumina bound catalyst, no evidence of Pt was found on the zeolite when examined by EDS. Pt was found only on the alumina binder. For the silica bound catalyst, particles of Pt were found only on the zeolite.

These results indicate that aluminum acts as a binding site for the Pt and removes Pt from the zeolite and demonstrate the advantages of silica over alumina as binder material for an aluminum-silicon-germanium zeolite on which platinum has been deposited. Silica as binding material allows the platinum to be redispersed so that its position and location within the catalyst, i.e., predominantly on the zeolite, not on the binding material, results in regenerated catalyst performance.

Figure 7:
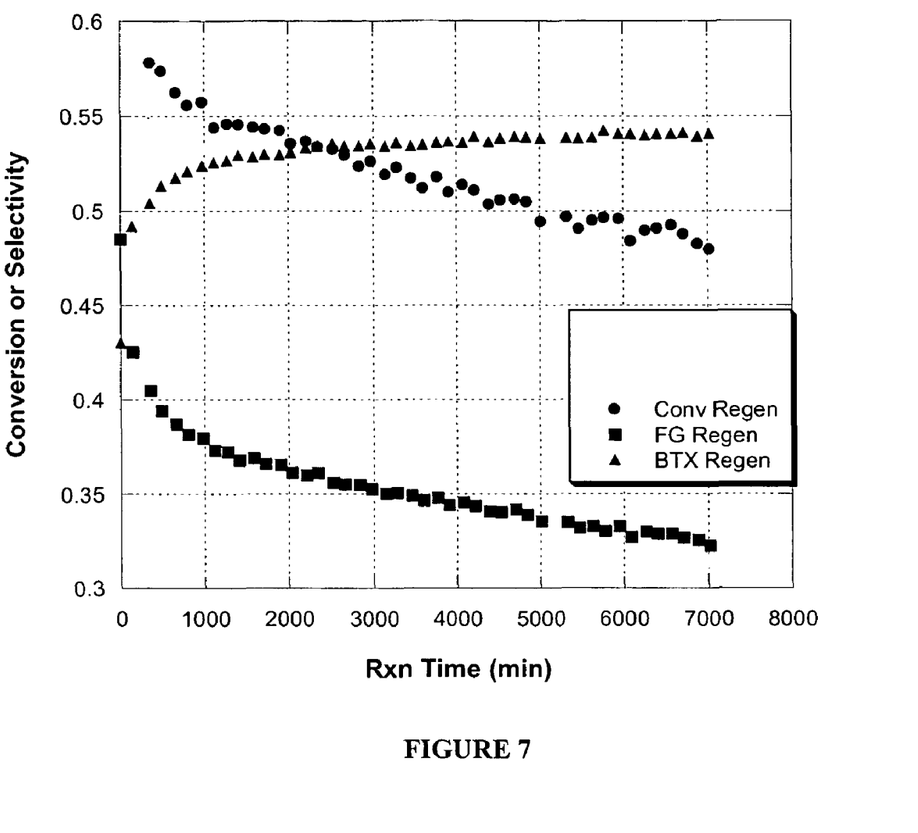
FIG. 7 shows BTX selectivity of a silica bound catalyst after regeneration
Figure 8:
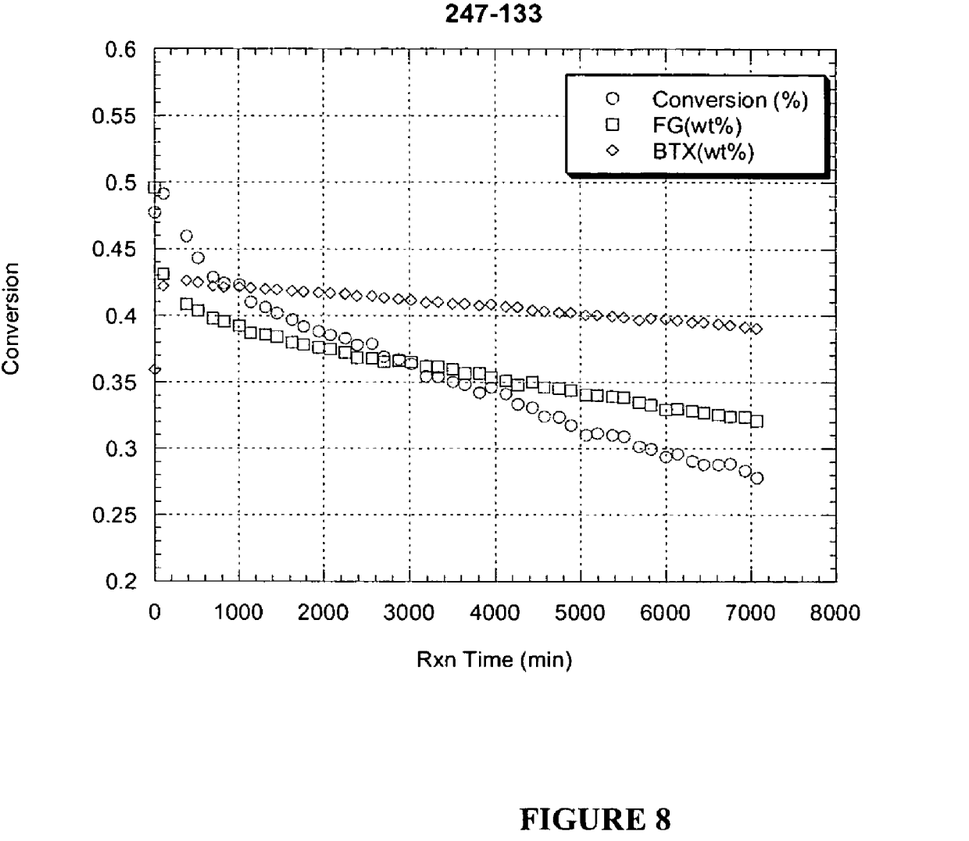
FIG. 8 shows BTX selectivity of an alumina bound catalyst after regeneration

FIGS. 7 and 8 demonstrate the difference in performance between silica bound and alumina bound catalysts processed at the regeneration conditions described above. The regenerated alumina bound catalyst had a loss of selectivity after being regenerated. It is believed that this decrease in catalyst performance may be attributed to the loss of platinum from the zeolite to the surrounding alumina binder demonstrated above.

Figure 9:
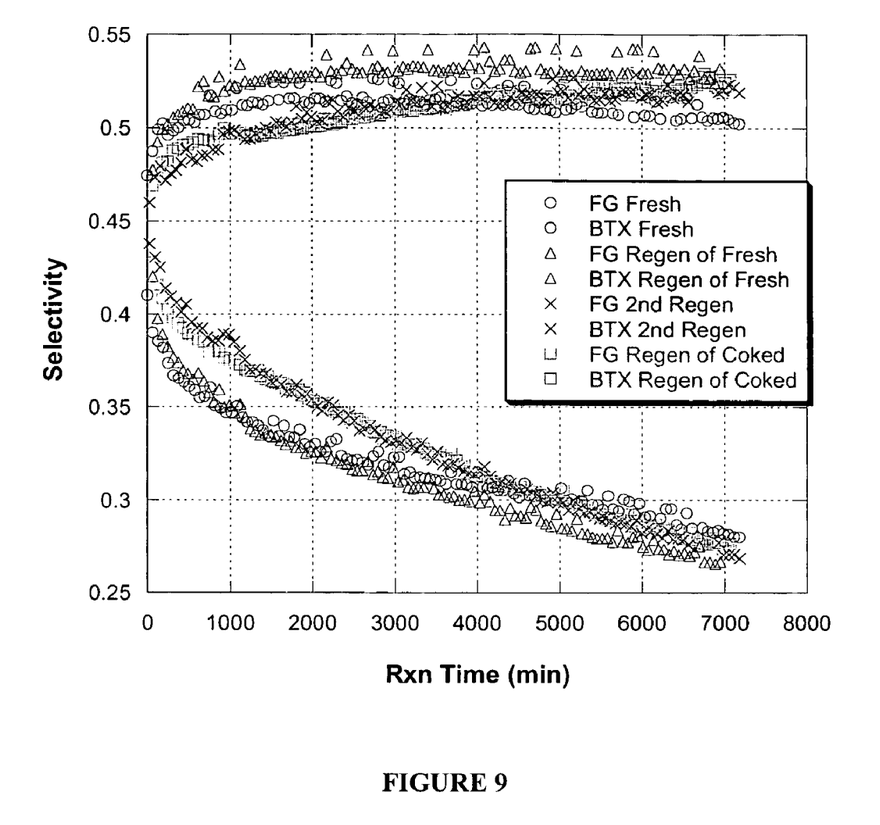
FIG. 9 shows BTX selectivity and fuel gas selectivity for a silica bound regenerated catalyst compared to a silica bound catalyst that has never been under reaction conditions, i.e., which has not been deactivated, but was processed at regeneration conditions.

A silica bound regenerated catalyst is compared in FIG. 9 with a silica bound catalyst that has never been under reaction conditions, i.e., which has not been deactivated, but was processed at the regeneration conditions described above. These results demonstrate that activity and selectivity can be recovered for a deactivated catalyst. Furthermore, the regenerated catalyst is stable and reproducible.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter of Patent of the United States of America is:

1. A process for the aromatization of hydrocarbons comprising:
   a) contacting a feedstock of one or more alkane(s) containing 2 to 8 carbon atoms per molecule with at least one catalyst containing an aluminum-silicon-germanium zeolite on which platinum has been deposited;
   b) recovering the aromatic product; and
   c) regenerating the catalyst by:
      1) contacting the catalyst first with a gaseous stream containing chlorine or a chlorine-containing compound, water and oxygen at partial pressures of about 0.014 psia to about 0.094 psia, about 0 psia to about 0.75 psia and about 0.14 psia to about 0.94 psia, respectively;
      2) contacting the catalyst second with a gaseous stream containing chlorine or a chlorine-containing compound, water and oxygen at partial pressures of about 0.014 psia to about 0.094 psia, about 0.015 psia to about 0.75 psia and about 0.2 psia to about 2.24 psia, respectively, wherein the partial pressure of oxygen in step 2) is higher than the partial pressure of oxygen in step 1);
      3) contacting the catalyst thirdly with a gaseous stream containing chlorine or a chlorine containing compound, water and oxygen at partial pressures of about 0.029 psia to about 0.37 psia, about 0 psia to about 0.19 psia and about 0.2 psia to about 2.24 psia, respectively, wherein the partial pressure of chlorine in step 3) is higher than the partial pressure of chlorine in step 2);
      4) steaming the catalyst with oxygen and water at partial pressures of about 0.2 psia to about 2.24 psia and about 0.029 psia to about 0.75 psia, respectively; and
      5) reducing the catalyst in hydrogen at a partial pressure of about 0.7 to about 19.7 psia.

2. The process for the aromatization of hydrocarbons as in claim 1 wherein step 1) is at a temperature from about 400° C. to about 550° C. for about 50 minutes to about twenty-four hours, step 2) is at a temperature from about 400° C. to about 550° C. for about 60 minutes to about 24 hours, step 3) is at a temperature in the range from about 400° C. to about 550° C. for about 60 minutes to about forty-eight hours, step 4) is at a temperature in the range from about 200° C. to about 550° C. for about 15 minutes to about twelve hours and step 5) is at a temperature in the range from 200° C. to 550° C. for about 30 minutes to about twenty-four hours.

3. The process for the aromatization of hydrocarbons as in claim 1 wherein in step 1) the partial pressures of chlorine, water and oxygen are about 0.014 psia to about 0.06 psia, about 0 psia to about 0.6 psia and about 0.14 psia to about 0.6 psia, respectively, in step 2), the partial pressures of chlorine, water and oxygen are about 0.014 psia to about 0.06 psia, about 0.15 psia to about 0.6 psia and about 0.2 psia to about 2.0 psia, respectively, step 3) the partial pressures of chlorine, water and oxygen are about 0.05 psia to about 0.3 psia, about 0.0 psia to about 0.15 psia and about 0.2 psia to about 2.0 psia, respectively, in step 4) the partial pressures of oxygen and water are about 0.5 psia to about 2.0 psia and about 0.15 psia to about 0.6 psia, respectively, in step 5) the partial pressure of hydrogen is about 0.7 to about 19.0 psia.

4. The process for the aromatization of hydrocarbons as in claim 3 wherein step 1) is at a temperature from about 425° C. to about 540° C. for about 50 minutes to about twenty hours, step 2) is at a temperature from about 425° C. to about 540° C. for about 1 hour to about twenty hours, step 3) is at a temperature in the range from about 425° C. to about 540° C. for about three hours to about twenty-four hours, step 4) is at a temperature in the range from about 425° C. to about 540° C. for about 30 minutes to about ten hours and step 5) is at a temperature in the range from 425° C. to 540° C. for about 30 minutes about eighteen hours.

5. The process for the aromatization of hydrocarbons as in claim 1 wherein in step 1) the partial pressures of chlorine, water and oxygen are about 0.014 psia to about 0.04 psia, about 0 psia to about 0.4 psia and about 0.14 psia to about 0.4 psia, respectively, in step 2) the partial pressures of chlorine, water and oxygen are about 0.014 psia to about 0.04 psia, about 0.15 psia to about 0.4 psia and about 0.4 psia to about 2.0 psia, respectively, in step 3) the partial pressures of chlorine, water and oxygen are about 0.1 psia to about 0.25 psia, about 0.0 psia to about 0.1 psia and about 0.4 psia to about 1.5 psia, respectively, in step 4) the partial pressures of oxygen and water are about 0.75 psia to about 1.75 psia and about 0.15 psia to about 0.4 psia, respectively, and in step 5) the partial pressure of hydrogen is about 0.8 to about 15.0 psia.

6. The process for the aromatization of hydrocarbons as in claim 5 wherein step 1) is at a temperature from about 450° C. to about 525° C. for about 1 hour to about sixteen hours, step 2) is at a temperature from about 450° C. to about 525° C. for about 1 hour to about sixteen hours, step 3) is at a temperature in the range from about 450° C. to about 525° C. for about three hours to about eighteen hours, step 4) is at a temperature in the range from about 450° C. to about 525° C. for about thirty minutes to about eight hours and step 5) is at a temperature in the range from 450° C. to 525° C. for about 30 minutes to about twelve hours.

7. The process for the aromatization of hydrocarbons as in claim 1 wherein at least 50% by weight of labile coke is removed in step 1) and essentially all of the remaining labile catalyst coke is removed is step 2).

8. The process for the aromatization of hydrocarbons as in claim 1 wherein the regenerated catalyst is additionally sulfided by:
   6) contacting the regenerated catalyst with a sulfur compound at a gas hourly space velocity of about 10 hr$^{-1}$ to about 8000 hr$^{-1}$ at a temperature range of about 25° C. to about 550° C.; and 7) contacting the sulfided catalyst with a stripping gas at hourly space velocity of about 10 hr$^{-1}$ to about 8000 hr$^{-1}$ at a temperature of about 25° C. to about 550° C.

9. The process for the aromatization of hydrocarbons as in claim 8 wherein the sulfur compound is hydrogen sulfide or an organosulfide compound.

10. The process for the aromatization of hydrocarbons as in claim 9 wherein the organosulfide compound is diethyl disulfide.

11. The process for the aromatization of hydrocarbons as in claim 8 wherein the stripping gas is a mixture of a stripping gas with an inert gas.

12. The process for the aromatization of hydrocarbons as in claim 11 wherein the inert gas is nitrogen, argon or helium.

13. The process for the aromatization of hydrocarbons as in claim 11 wherein the mixture of stripping gas with inert gas is in a mole/mole ratio of from about 1/99 to about 100/0.

14. The process for the aromatization of hydrocarbons as in claim 12 wherein the mixture of stripping gas with inert gas is in a mole/mole ratio of about 50/50.

15. The process for the aromatization of hydrocarbons as in claim 1 wherein the regenerated catalyst is additionally sulfided by contacting the regenerated catalyst with a sulfur compound in the feedstock.

16. The process for the aromatization of hydrocarbons as in claim 1 wherein the zeolite structure is MFI, FAU, TON, MFL, VPI, MEL, AEL, AFI, MWW or MOR.

17. The process for the aromatization of hydrocarbons as in claim 16 wherein the zeolite structure is MFI.

18. The process for aromatization of hydrocarbons as in claim 1 wherein the Si/Al ratio is in excess of 35:1.

19. The process for aromatization of hydrocarbons as in claim 1 wherein the Si/Al ratio is from 35 to 60.

20. The process for aromatization of hydrocarbons as in claim 1 wherein the Si/Al ratio is from 45 to 55.

21. The process for aromatization of hydrocarbons as in claim 1 wherein the silicon/germanium to aluminum atomic ratio (Si—Ge:Al) is greater than 25:1.

22. The process for aromatization of hydrocarbons as in claim 1 wherein the silicon/germanium to aluminum atomic ratio is in the range from 45:1 to 250:1.

23. The process for aromatization of hydrocarbons as in claim 1 wherein the silicon/germanium to aluminum atomic ratio is in the range from 50:1 to 100:1.

24. The process for aromatization of hydrocarbons as in claim 1 wherein platinum is present in the range from 0.05% to 3% by weight.

25. The process for aromatization of hydrocarbons as in claim 1 wherein platinum is present in the range from 0.2% to 2% by weight.

26. The process for aromatization of hydrocarbons as in claim 1 platinum is present in the range from 0.2 to 1.5% by weight.

27. The process for aromatization of hydrocarbons as in claim 1 wherein the catalyst is bound with an inert material which does not act as a binding site for platinum during the regeneration process.

28. The process for aromatization of hydrocarbons as in claim 1 wherein the inert material is silica, sulfated alumina, clay or zeolite bound zeolites.

29. The process for aromatization of hydrocarbons as in claim 1 wherein the catalyst is bound with silica.

30. The process for aromatization of hydrocarbons as in claim 1 wherein the alkane(s) contain 2 to 4 carbon atoms per molecule.

31. The process for aromatization of hydrocarbons as in claim 1 wherein the alkane(s) contain 6 to 8 carbon atoms per molecule.

32. A process for regenerating a catalyst containing an aluminum-silicon-germanium zeolite on which platinum has been deposited comprising:
   a) contacting the catalyst first with a gaseous stream containing chlorine or a chlorine-containing compound, water and oxygen at partial pressures of about 0.014 psia to about 0.094 psia, about 0 psia to about 0.75 psia and about 0.14 psia to about 0.94 psia, respectively;
   b) contacting the catalyst second with a gaseous stream containing chlorine or a chlorine-containing compound, water and oxygen at partial pressures of about 0.014 psia to about 0.094 psia, about 0.015 psia to about 0.75 psia and about 0.2 psia to about 2.24 psia, respectively, wherein the partial pressure of oxygen in step b) is higher than the partial pressure of oxygen in step a);
   c) contacting the catalyst thirdly with a gaseous stream containing chlorine or a chlorine containing compound, water and oxygen at partial pressures of about 0.029 psia to about 0.37 psia, about 0 psia to about 0.19 psia and about 0.2 psia to about 2.24 psia, respectively, wherein the partial pressure of chlorine in step c) is higher than the partial pressure of chlorine in step b);
   d) steaming the catalyst with oxygen and water at partial pressures of about 0.2 psia to about 2.24 psia and about 0.029 psia to about 0.75 psia, respectively; and
   e) reducing the catalyst in hydrogen at a partial pressure of about 0.7 to about 19.7 psia.

33. The process for regenerating the catalyst as in claim 32 wherein step a) is at a temperature from about 400° C. to about 550° C. for about 50 minutes to about twenty-four hours, step b is at a temperature from about 400° C. to about 550° C. for about 60 minutes to about 24 hours, step c is at a temperature in the range from about 400° C. to about 550° C. for about 60 minutes to about forty-eight hours, step d is at a temperature in the range from about 200° C. to about 550° C. for about 15 minutes to about twelve hours and step e is at a temperature in the range from 200° C. to 550° C. for about 30 minutes to about twenty-four hours.

34. The process for regenerating the catalyst as in claim 32 wherein in step a) the partial pressures of chlorine, water and oxygen are about 0.014 psia to about 0.06 psia, about 0 psia to about 0.6 psia and about 0.14 psia to about 0.6 psia, respectively, in step b), the partial pressures of chlorine, water and oxygen are about 0.014 psia to about 0.06 psia, about 0.15 psia to about 0.6 psia and about 0.2 psia to about 2.0 psia, respectively, in step c) the partial pressures of chlorine, water and oxygen are about 0.05 psia to about 0.3 psia, about 0.0 psia to about 0.15 psia and about 0.2 psia to about 2.0 psia, respectively, in step d) the partial pressures of oxygen and water are about 0.5 psia to about 2.0 psia and about 0.15 psia to about 0.6 psia, respectively, in step e) the partial pressure of hydrogen is about 0.7 to about 19.0 psia.

35. The process for regenerating the catalyst as in claim 34 wherein step a) is at a temperature from about 425° C. to about 540° C. for about 50 minutes to about twenty hours, step b) is at a temperature from about 425° C. to about 540° C. for about 1 hour to about twenty hours, step c) is at a temperature in the range from about 425° C. to about 540° C. for about three hours to about twenty-four hours, step d) is at a temperature in the range from about 425° C. to about 540° C. for about 30 minutes to about ten hours and step e) is at a temperature in the range from 425° C. to 540° C. for about 30 minutes about eighteen hours.

36. The process for regenerating the catalyst as in claim 32 wherein in step a) the partial pressures of chlorine, water and oxygen are about 0.014 psia to about 0.04 psia, about 0 psia to about 0.4 psia and about 0.14 psia to about 0.4 psia, respectively, in step b) the partial pressures of chlorine, water and oxygen are about 0.014 psia to about 0.04 psia, about 0.15 psia to about 0.4 psia and about 0.4 psia to about 2.0 psia, respectively, in step c) the partial pressures of chlorine, water and oxygen are about 0.1 psia to about 0.25 psia, about 0.0 psia to about 0.1 psia and about 0.4 psia to about 1.5 psia, respectively, in step d) the partial pressures of oxygen and water are about 0.75 psia to about 1.75 psia and about 0.15 psia to about 0.4 psia, respectively, and in step e) the partial pressure of hydrogen is about 0.8 to about 15.0 psia.

37. The process for regenerating the catalyst as in claim 36 wherein step a) is at a temperature from about 450° C. to about 525° C. for about 1 hour to about sixteen hours, step b) is at a temperature from about 450° C. to about 525° C. for about 1 hour to about sixteen hours, step c) is at a temperature in the range from about 450° C. to about 525° C. for about three hours to about eighteen hours, step d) is at a temperature in the range from about 450° C. to about 525° C. for about thirty minutes to about eight hours and step e) is at a temperature in the range from 450° C. to 525° C. for about 30 minutes to about twelve hours.

38. The process for regenerating the catalyst as in claim 32 wherein at least 50% by weight of labile coke is removed in step a) and essentially all of the remaining labile catalyst coke is removed is step b).

39. The process for regenerating the catalyst as in claim 32 wherein the regenerated catalyst is additionally sulfided by:
f) contacting the regenerated catalyst with a sulfur compound at a gas hourly space velocity of about 10 hr$^{-1}$ to about 8000 hr$^{-1}$ at a temperature range of about 25° C. to about 550° C.; and
g) contacting the sulfided catalyst with a stripping gas at hourly space velocity of about 10 hr$^{-1}$ to about 8000hr$^{-1}$ at a temperature of about 25° C. to about 550° C.

40. The process for regenerating the catalyst as in claim 39 wherein the sulfur compound is hydrogen sulfide or an organosulfide compound.

41. The process for regenerating the catalyst as in claim 40 wherein the organosulfide compound is diethyl disulfide.

42. The process for regenerating the catalyst as in claim 39 wherein the stripping gas is a mixture of a stripping gas with an inert gas.

43. The process for regenerating the catalyst as in claim 42 wherein the inert gas is nitrogen, argon or helium.

44. The process for regenerating the catalyst as in claim 42 wherein the mixture of stripping gas with inert gas is in a mole/mole ratio of from about 1/99 to about 100/0.

45. The process for regenerating the catalyst as in claim 43 wherein the mixture of stripping gas with inert gas in a mole/mole ratio of about 50/50.

46. The process for regenerating the catalyst as in claim 32 wherein the regenerated catalyst is additionally sulfided by contacting the regenerated catalyst with a sulfur compound in a feedstock.

47. The process for regenerating a catalyst as in claim 32 wherein the zeolite structure is MFI, FAU, TON, MFL, VPI, MEL, AEL, AFI, MWW or MOR.

48. The process for regenerating a catalyst as in claim 47 wherein the zeolite structure is MFI.

49. The process for regenerating a catalyst as in claim 32 wherein the Si/Al ratio is in excess of 35:1.

50. The process for regenerating a catalyst as in claim 49 wherein the Si/Al ratio is from 35 to 60.

51. The process for regenerating a catalyst as in claim 50 wherein the Si/Al ratio is from 45 to 55.

52. The process for regenerating a catalyst as in claim 32 wherein the silicon/germanium to aluminum atomic ratio (Si—Ge:Al) is greater than 25:1.

53. The process for regenerating a catalyst as in claim 32 wherein the silicon/germanium to aluminum atomic ratio is in the range from 45:1 to 250:1.

54. The process for regenerating a catalyst as in claim 53 wherein the silicon/germanium to aluminum atomic ratio is in the range from 50:1 to 100:1.

55. The process for regenerating a catalyst as in claim 32 wherein platinum is present in the range from 0.05% to 3% by weight.

56. The process for regenerating a catalyst as in claim 55 wherein platinum is present in the range from 0.2% to 2% by weight.

57. The process for regenerating a catalyst as in claim 56 wherein platinum is present in the range from 0.2 to 1.5% by weight.

58. The process for regenerating a catalyst as in claim 57 wherein the catalyst is bound with an inert material which does not act as a binding site for platinum during the regeneration process.

59. The process for regenerating a catalyst as in claim 32 wherein the inert material is silica, sulfated alumina, clay or zeolite bound zeolites.

60. The process for regenerating a catalyst as in claim 32 wherein the catalyst bound is with silica.

* * * * *